United States Patent
Hawa

(10) Patent No.: US 11,607,235 B2
(45) Date of Patent: Mar. 21, 2023

(54) ENDOSURGICAL EXTRACTION BAG FOR COLLECTION OF LARGE SPECIMEN

(71) Applicant: Nadim Hawa, Ashburn, VA (US)

(72) Inventor: Nadim Hawa, Ashburn, VA (US)

(73) Assignee: Nadim Nicolas Hawa, Ashburn, VA (US)

( * ) Notice: Subject to any disclaimer, the term of this patent is extended or adjusted under 35 U.S.C. 154(b) by 267 days.

(21) Appl. No.: 17/143,047

(22) Filed: Jan. 6, 2021

(65) Prior Publication Data
US 2022/0211399 A1    Jul. 7, 2022

(51) Int. Cl.
```
A61B 17/221    (2006.01)
A61B 17/42     (2006.01)
A61B 17/22     (2006.01)
A61B 34/20     (2016.01)
G06T 7/00      (2017.01)
G06T 7/11      (2017.01)
G06T 19/00     (2011.01)
G06T 19/20     (2011.01)
```
(52) U.S. Cl.
CPC ............ *A61B 17/221* (2013.01); *A61B 17/42* (2013.01); *A61B 34/20* (2016.02); *A61B 2017/2212* (2013.01); *A61B 2017/22051* (2013.01); *A61B 2017/4216* (2013.01); *G06T 7/0012* (2013.01); *G06T 7/11* (2017.01); *G06T 19/006* (2013.01); *G06T 19/20* (2013.01)

(58) Field of Classification Search
None
See application file for complete search history.

(56) References Cited

U.S. PATENT DOCUMENTS

| | | | | |
|---|---|---|---|---|
| 5,480,404 A | * | 1/1996 | Kammerer | A61B 17/00234 606/127 |
| 7,650,887 B2 | * | 1/2010 | Nguyen | A61B 17/3423 128/889 |
| 9,789,268 B2 | * | 10/2017 | Hart | A61B 10/04 |
| 10,932,767 B2 | * | 3/2021 | Naga Kalepu | A61B 17/0218 |
| 11,369,352 B2 | * | 6/2022 | Baril | A61B 17/00234 |
| 2007/0179458 A1 | * | 8/2007 | Leroy | A61B 17/00234 383/61.4 |
| 2011/0190781 A1 | * | 8/2011 | Collier | A61B 17/00234 606/114 |
| 2012/0277758 A1 | * | 11/2012 | Davis | A61B 17/00234 606/114 |
| 2016/0100857 A1 | * | 4/2016 | Wachii | A61B 17/3423 600/204 |
| 2020/0268410 A1 | * | 8/2020 | Yaari | A61B 17/3439 |
| 2021/0378647 A1 | * | 12/2021 | Baril | A61B 17/00234 |

* cited by examiner

*Primary Examiner* — Nancy Bitar

(57) ABSTRACT

Provided is an intra-abdominal tissue retrieval bag. The bag has an inflated state and a deflated state. The bag is introduced into the abdomen in a deflated state through a small incision and placed underneath the specimen to be retrieved. The bag is defined by an inflatable defining circumferential ring at the opening and an inflatable collection sac. Both inflated using external pneumo source sequentially, the same that is used to maintain pneumoperitoneum during laparoscopic surgery. After insufflation, the specimen becomes fully contained and ready for retrieval after desufflation.

7 Claims, 2 Drawing Sheets

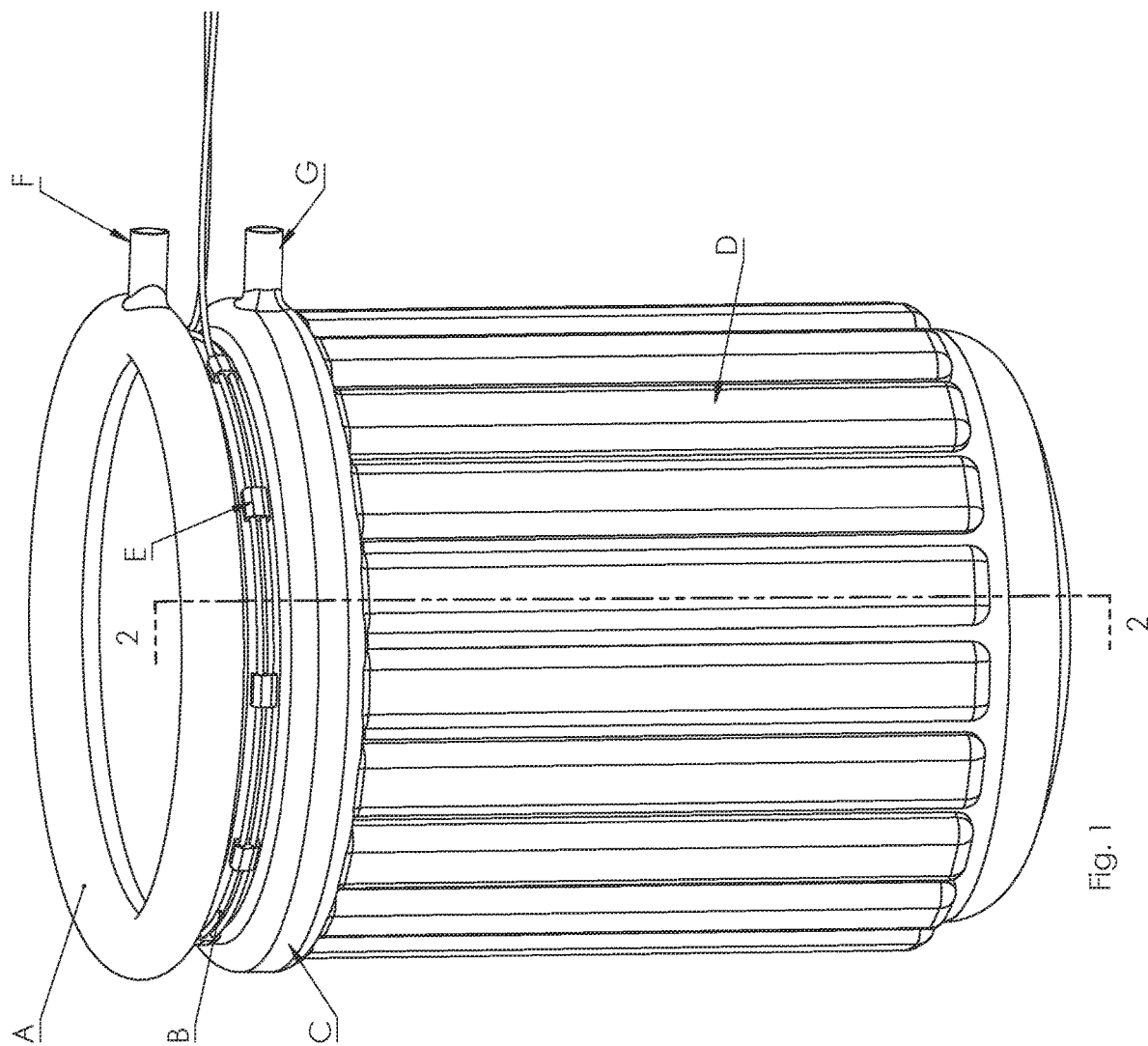
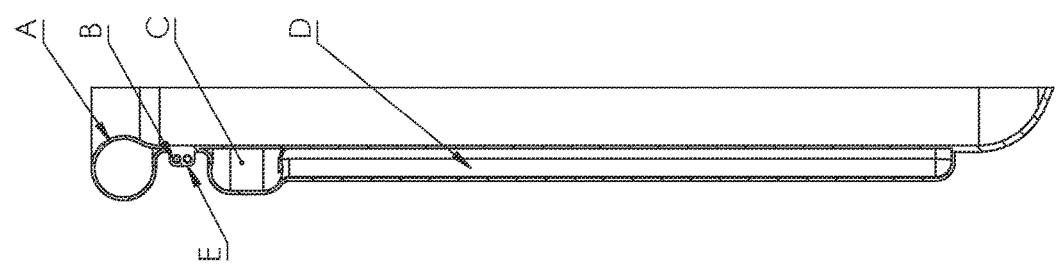

ENDOSURGICAL EXTRACTION BAG FOR COLLECTION OF LARGE SPECIMEN

BACKGROUND OF THE INVENTION

Endosurgical extraction bags are challenging when using in massive tissue or specimens. Accordingly there is an ongoing need for an Endosurgical extraction bag that makes it easier for the surgeon to "bag" the specimen. Due to a novel and unique ability to be inflated and be distended, a bag allows and accommodates for small, medium size and massive specimens. That would also provide comfort to the patient in an operational mode by minimizing operative time, less intra abdominal pressure time and instrument manipulation during laparoscopic and robotic surgery.

This invention relates to a surgical tissue specimen bag and a method of retrieving tissue from the abdominal cavity in the era of minimally invasive surgery and the rise in the use of laparoscopic assisted surgeries and robotic assisted laparoscopic surgeries. There is a need to retrieve specimens without making a big surgical incision. An important requirement of such an extraction bag is that the tissue collected in the bag cannot escape before the extraction bag is withdrawn from the body.

Typically, the laparoscopic and robotic operating arms are anything from 5 to 12 mm in diameter. Any specimen larger than that would be difficult to extract without morcellation. By morcellation we mean cutting the tissue into smaller pieces in order to be extracted and that risks spillage of specimen and fluid into the abdominal cavity which can lead to parasitic tissue growth or upgrading in the staging of cancers; hence the need for tissue retrieval bags that are reliable and prevent spillage. Once the specimen is secured in the bag, then morcellation in any contained fashion is possible.

Many tissue retrieval bags are currently being used in surgery. It has always been a challenge how to put big specimens inside a collection bag in view of the awkward positioning of the patient during surgery (lithotomy) and the limitation of the intra abdominal space. Other difficulties include:
1—Other organs like bowel being in the way
2—Inability to maintain pneumoperitoneum (air in the abdominal cavity during surgery)
3—Size of specimen bigger than the lens's field of visualization
4—Surgeon's inexperience in placing the specimen inside the Endoscopic retrieval bag
5—Lack of coordination between surgeon and assistant
6—Specimen is sometimes too large. The surgeon need to bag the specimen while looking opposite to the visual field
7—Irregularity and non uniformity of specimens like fibroids and uterus
8—Heavy specimens like calcified fibroid that can not be lifted easily by the use of laparoscopic or robotic devices/arms
9—A further disadvantage of the known extraction bags is that they are unnecessarily large, rigid, and relatively non-compliant, and nondistensible Tissue extraction can consume sometimes up to 45 minutes or one hour and and that leads to increased operative time and cost and many times lead to abortion of the containment and hands morcellation by the surgeon without containment.

Many of the laparoscopic procedures include the removal of large internal organs such as uterus, fibroids, ovaries and ovarian cysts, bowel, kidney, and various intra abdominal benign and malignant tumors. Currently, there are several ways to remove an intra abdominal mass from the abdominal cavity. One way is by creating an incision in the abdominal wall that allows the removal of the mass. This converts the procedure to a laparotomy or mini-laparotomy with the unattended disadvantages of open surgery. Another way is by removing the mass through the cul-de-sac, by performing an incision at the vaginal apex (culdotomy). This disadvantageously requires another incision and also has the disadvantages of increased injury and infection. A third way is by draining the cystic mass and then removing the cyst capsule through one of the laparoscopy ports. The disadvantage of this method is the risk of spillage of the cyst contents. A fourth method of removing the mass is by cutting the large solid mass to smaller particles inside the abdomen and removing the particles through one of the laparoscopy ports or through a culdotomy. Such cutting known as morcellation can be achieved manually or by laparoscopic power cutting devices which have the disadvantages of scattering tissue in the abdominal cavity and injury to the abdominal organs by the cutting devices. The FDA continues to recommend limiting the use of laparoscopic power morcellation in women undergoing myomectomy or hysterectomy. In addition, FDA recommends that when morcellation is appropriate, only contained morcellation be performed.

DESCRIPTION OF RELATED ART

Endoscopic retrieval bags were patented and some made it to development and to production phases and currently on the market.

U.S. patent Oprey et al (U.S. Pat. No. 9,370,378B2) teaches a method of retrieving a tissue specimen comprising inserting a surgical retrieval apparatus through an opening in a patient's skin, the surgical retrieval apparatus including a support member and a retrieval bag extending from the support member and having an opening to receive the tissue specimen. A net is introduced into the retrieval bag and placed over the tissue specimen. The net and retrieval bag are removed from the patient's body to remove the tissue specimen.

U.S. patent for Desai et al (U.S. Pat. No. 10,653,400) teaches a specimen retrieval system, comprising: a bag having a flexible basket with an opening configured to be deployable for receiving a tissue specimen, and an elongate string encircling the flexible basket and extending therefrom to terminate remote from the flexible basket, the string being operable to close the opening of the flexible basket; an outer cannula having a distal end and a proximal end with a cannula handle located at the proximal end of the outer cannula, the outer cannula having a lumen configured to receive the bag therein and to permit passage of the bag through the distal end of the outer cannula for deployment of the bag.

U.S. patent for Taylor, Thrun (U.S. Pat. No. 9,974,528B2) teaches a tissue retrieval bag defined by a region of the bag defining an opening; and exterior surface of the bag depending from the opening; and a channel formed into the exterior surface of the bag, wherein the channel provides access to the interior of the bag through the exterior surface.

U.S. patent for Riek et al (U.S. Pat. No. 5,788,709) teaches a flexible bag is introduced into the abdominal cavity to remove larger portions of tissue from the abdominal cavity through a threaded casing introduced into the abdominal wall. The bag features a side opening through which the tissue can be moved into the bag. The end opening of the bag remains extracorporeal to the threaded casing.

After pulling out the bag the side opening is located outside of the threaded casing and the tissue is tightly enclosed by the portion of the bag remaining in the abdominal cavity and is accessible for cutting up the tissue form outside, through the threaded casing.

U.S. patent application publication for Gharb et al (US 2011/0301459) teaches a bag has a reaching and manipulating unit for reaching and manipulating a sterile surgical instrument housed within a sterile interior space, where the bag is made of transparent material. A top surface and a bottom surface define the sterile interior space. The manipulating unit comprises an opening in the bag for insertion of hand into the bag. The opening comprises an engaging unit for engaging the hand to prevent moving hand out and back into the sterile space. A sleeve is attached to the opening, and a sterile surgical glove is affixed to the opening.

Chinese Application CN 106994026 A titled "Intra-abdominal controllable bag opening" discloses an intra-abdominal controllable bag opening and closing device. Two linking ropes are bound in a hole at the front end of pliers. A bag is adhered to the front end of the pliers and two linking ropes by an adhesive plaster. While the bag passes through an abdominal hole of a patient, the rear part of the pliers is clamped, so the front part of the pliers (1-1) is clamped too, the bag is inserted into the abdominal cavity from the abdominal hole of the patient, the bag is moved to the needed position, and the rear part of the pliers is opened by hands, so that the front part of the pliers is opened too, and the bag is opened. The needed tissue is placed in the bag, the pliers are clamped, so the bag is closed. Through the above method, in laparoscopic surgery, a doctor can conveniently and rapidly put the cut patient tissue in the bag because the opening part of the bag is larger and the bag has a certain intensity, and the bag can carry more substances.

U.S. patent for Johnson et al (U.S. Pat. No. 9,522,034) teaches a tissue removal system for extracting a tissue specimen from a patient. The system has a retrieval bag, a first electrode, and a return electrode. The retrieval bag has a flexible container with an opening. The first electrode is coupled to an interior of the flexible container, and has a conductive wire with an exposure area, a first load-bearing area, a coating having a first active electrode surface area, and an impedance that is greater than an impedance of the conductive wire. The first active electrode surface area is less than the exposure area. The coating is configured to degrade during application of electrosurgical power and wherein the degradation expands the first active electrode surface area during the application of the electrosurgical power. However, until now, there hasn't been any system that is reliable, reproducible, operator friendly, cheap, less time consuming, and safe. Therefore there was a need for an Endosurgical extraction bag for collecting large specimens after Endoscopic surgery that offers all these advantages.

SUMMARY OF THE INVENTION

The endosurgical extraction bag proposed has the advantage of being inflated in the abdominal cavity in a simple and reliable manner using a normal insufflator tubing that is already maintaining pneumoperitoneum during surgery. Note that pneumoperitoneum is the presence of air or other gas in the peritoneal cavity, a potential space within the abdominal cavity.

It is a simple, low cost retrieval bag. Rather than putting the specimen in the bag, which is tedious and extremely time consuming for large and irregular shaped specimens, we bring the bag under the uterus:

1—The surgical extraction bag is brought to and under the specimen by the surgeon using laparoscopic tools like graspers. It is initially in a deflated state under the specimen in a non-specific way 2—Through a thin tubing, insufflation is applied to a circumferential rim. Gradually the rim fills with air and expands horizontally circumferentially around the specimen and delineates the borders of the specimen 3—Through a separate thin tubing, insufflation is applied to a connected vertical air channel tunnel on the side of the bag to elevate the bag and engulf the specimen. The best description is the infant bouncer in a deflated and inflated state.

4—Once the specimen is completely engulfed, both air channels are deflated and the opening is cinched manually by a thin circumferential thread to close on and inundate the specimen to be ready for retrieval through an opening in the abdominal wall.

The advantages of the Endosurgical extraction bag proposed is the structure and design that make it easier for the surgeon to "bag" the specimen. Due to its ability to be inflated and be distended, it allows and accommodates for small, medium size and massive specimens. That would also provide comfort to the patient in an operational mode by minimizing operative time, less intra abdominal pressure time and instrument manipulation.

BRIEF DESCRIPTION OF THE DRAWINGS

Various embodiments of the invention are disclosed in the following detailed description and the accompanying drawings.

FIG. 1 is a view of an endosurgical extraction bag, showing our new design. The view of an endosurgical extraction bag including Horizontal Air Rim A; B retrieval String for closure state; C channel for the vertical air column; D vertical air column; E the Tunnel housing the cinching string; F is the air introducing tube for the horizontal rim; G is the air introducing tube for the vertical rim; FIG. 2 is cross sectional view FIG. 2: Cross sectional view of the endosurgical extraction bag.

DETAILED DESCRIPTION

Figure 3:
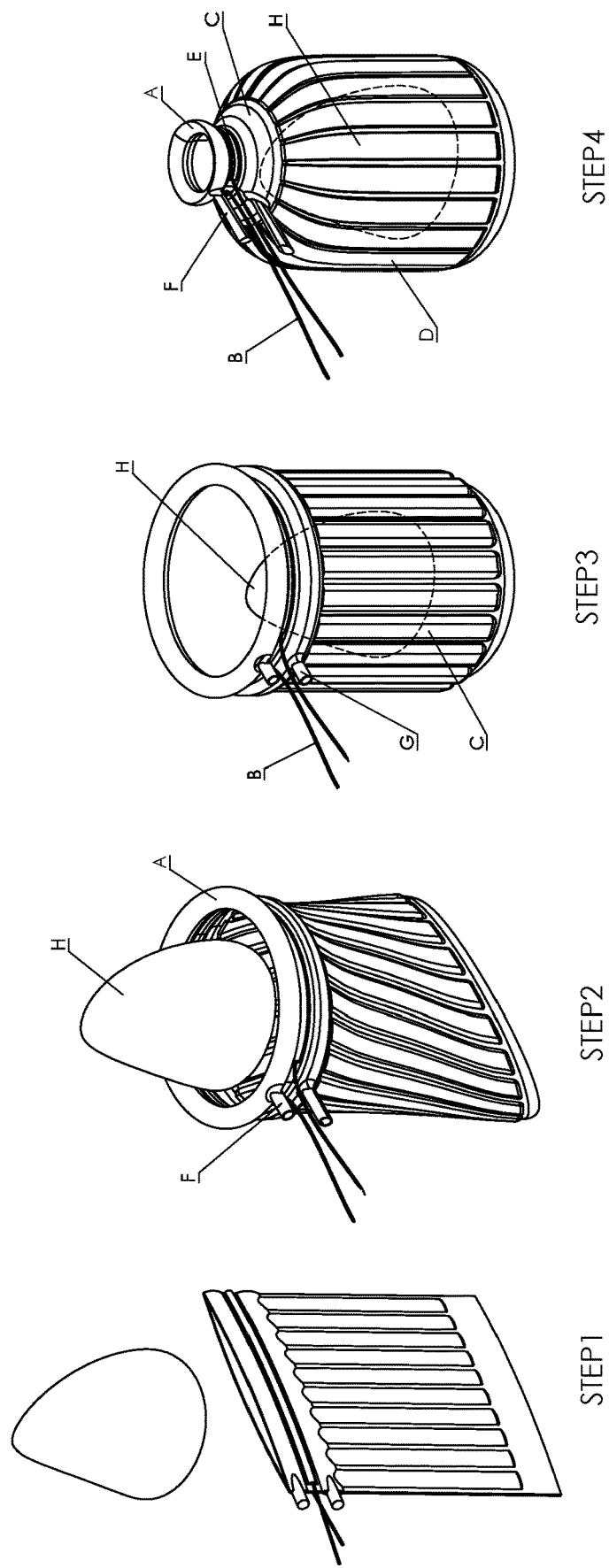
FIG. 3: Overall view of the Endosurgical Extraction Bag. Step 1: A deflated natural state of the endosurgical extraction bag Step 2: The circumferential horizontal rim at an inflated state including the Specimen H Step 3: The vertical air column beginning to inflate and rise up Step 4: The horizontal air tunnels at a full inflated state engulfing the specimen H Step 5: The endosurgical extraction bag rim reaches a closured state after the deflation state.

A broad aspect of some embodiments of the invention relates to an endosurgical distensible extraction bag or pouch, which may be inserted into the body (e.g., a body lumen such as the abdominal cavity, thoracic cavity) and used for processing body tissue therein, while inside the body. Alternatively, the processing comprises division of solid tissue (such as a tumor) into pieces, which can then be removed or other size reduction method applied to tissue, prior to tissue removal from the body, such that the workspace device ultimately acts as a retrieval device. In some embodiments, the tissue includes separating a small portion of tissue from a mass of tissue, the small portion being sufficiently small in size to be laparoscopically removed.

In accordance with one aspect of some embodiments of the present invention, an endosurgical extraction bag for collecting large specimens or body tissue or body fluid after endoscopic surgery is provided. It comprises an:

1—Insertion step that inserts a deflated collection retrieval pouch/bag through a small artificially created or natural opening into an abdominal cavity, the deflated collection-retrieval pouch/bag main part formed of a circumferential horizontal rim and a vertical air tunnel shafts.

2—While abdominal pneumoperitoneum is maintained, bringing and positioning of the deflated collection retrieval pouch/bag by the surgeon in a nonspecific orientation in the abdominal cavity as long as it is lying beneath the specimen.

3—An inflating step that inflates, using a small air introducing tube, the circumferential horizontal rim in order to EXPAND and DEFINE and engulf a width dimension of the large specimen; and then inflates, using a second air introducing tube, the vertical air tunnel in order to EXPAND and contain a vertical dimensions of the large specimen 4—Deflating the bag stage by allowing the air in both tunnels to escape 5—A closure step that pulls a retrieval string housed in the horizontal opening ring to reach a closure or actuation state at the opening of the endosurgical extraction bag after the deflation natural state allowing full containment of the large specimen in order to remove out of a human body through contained morcellation.

In a typical laparoscopic or Robotic surgery, and after the blood supply is secured and the specimen is resected/detached and now lying free in the abdominal cavity. The bag is placed under the specimen without any specific orientation. The insufflating tubes that are providing pneumoperitoneum during the surgery are removed from the insufflating trocar that is used to introduce instruments during laparoscopic surgery and are attached to a thin tubing that leads to the air introducing tube for the horizontal rim (F) as seen in FIG. 1. Once the air enters the circumferential rim A in FIG. 3 step 1 it expands as much as needed to surround the whole specimen as seen in step 2. The same insufflating tube is then removed from tubing F and is attached to a thin tubing that leads to the air introducing tube for the vertical rim (G). Once the air flow enters tunnel C, it continues to vertical channels D in FIG. 3 step 3 and leads to the gradual vertical expansion of the bag surrounding and enclosing the specimen completely as shown in step 4. Note that the air flow entering the bag through port F and port G controls the amount of pressure introduced into tubings A and C and that is controlled by the surgeon as needed to visually contain the specimen in a proper position inside the bag. Note that an optional indicator can visually show the surgeon that the bag is in a proper position when deployed. In step 5, the specimen is secured in the bag, all the air flow is let out the tubes and the bag is cinched secure by a retrieval String B that is housed in between tube A and C. Once the bag is closed securely, it can be brought to any opening in the cavity that we are operating in, whether it is the abdominal cavity (umbilical, colpotomy), or the thoracic cavity and then the specimen is securely morcellated in a multitude of ways including manual morcellation or power morcellation.

We describe a system that is reliable, reproducible, operator friendly, cheap, less time consuming, and safe. Therefore there was a need for an Endosurgical extraction bag for collecting large specimens after Endoscopic surgery that offers all these advantages.

In accordance with another aspect of the invention the endoscopic bag can be inserted into the abdominal cavity in a multitude of ways including, vaginal, and oral through the gastric wall. In a more commonly performed way, an abdominal incision is done at the level of the belly button between 1-3 inches. that incision is carried down to the underlying fascia. The fascia is incised and extended vertically or horizontally by the use of energy monopolar cut. The peritoneum is identified and tended up and incised accordingly. An Alexis O wound protractor/retractor (Applied medical) is applied into the incision and deployed in order to expand the incision enough to deploy the proposed endoscopic bag into the abdominal cavity. A laparoscopic cap (Applied Medical) is used to seal the protractor rim in order to re-establish pneumoperitoneum and complete the second stage of placing the deflated endoscopic bag under the specimen. After the complete containment of the bag, the cap is removed and the bag is brought to the outside of the abdominal cavity by the retrieval string that was used to cinch the rim of the endoscopic bag. Once the edges of the bag are out of the abdominal cavity, manual or power morcellation can be performed to extract the specimen in a contained fashion.

In some embodiments, the pouch is made of an elastic bag of a variety of tensile strength to accommodate a variety of tissue types with different shapes and rigidity wherein the shape of the large specimen or tissues is large and irregular. A massive fibroid uterus or a large adnexal mass whether solid or cystic can be placed effortlessly in the proposed bag and it can distend to accommodate accordingly by varying the degree and amount of insufflation (pressure and flow rate).

In some embodiment of the invention, it can also be used in other body anatomical spaces like the thoracic cavity to accommodate different types of masses/tumors. It presents a major advantage in the thoracic cavity since the potential space is extremely limited and less distensible compared to the abdominal cavity.

In some embodiments, the gas inflated can be changed to have different densities or can be changed to contain fluids such as saline or any other fluid. The bag is designed to facilitate morcellation through "paper roll" manual technique. In another embodiment, power morcellation can be introduced into the bag to allow the cutting of specimens into smaller pieces.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The terms "comprises", "comprising", "includes", "including", "having" and their conjugates mean "including but not limited to". The term "consisting of" means "including and limited to". It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An endosurgical extraction bag for collecting a large specimen or body fluid that is used in particular in endoscopic interventions in a human or animal body that are performed through a small artificially created or a natural opening, comprising:
    inserting a deflated collection retrieval pouch or bag through the small artificially created or natural opening into an abdominal or thoracic cavity,
    retrieving the large specimen using the deflated collection-retrieval pouch or bag that is brought in a deflated natural state;
    wherein the deflated collection-retrieval pouch or bag main part formed of a circumferential horizontal rim and a vertical air tunnel channels;
    inflating using first an air introducing tube that leads to the circumferential horizontal rim in order to define and engulfs a width dimensions of the large specimen,
    inflating using a second air introducing tube that lead air to the vertical air tunnel channels in order to engulfs a vertical dimensions of the large specimen;
    maintaining a pneumo peritoneum stage of the abdominal cavity;
    pulling a retrieval string to reach a closure or actuation state at the end of the endosurgical extraction bag after the deflation natural state; and allowing extraction of the large specimen out of the human or animal body.

2. The endosurgical extraction bag according to claim 1, wherein a shape of the large specimen is large and irregular that includes at least a massive fibroid uterus or a large adnexal mass.

3. The endosurgical extraction bag according to claim 2, wherein the large specimen includes at least one of the following: uterus, fibroids, ovaries and ovarian cysts, bowel, kidney, lung, and various intra abdominal and intrathoracic benign and malignant tumors.

4. The endosurgical extraction bag according to claim 1, wherein the air entering the deflated collection retrieval pouch/bag through the first air introducing tube and second air introducing tube sequentially controls an amount of pressure introduced into the horizontal tunnel and the vertical air column channels and that is controlled by a surgeon to visually contain the large specimen or body fluid in a proper position inside the endosurgical extraction bag.

5. The endosurgical extraction bag according to claim 4, wherein the large specimen is secured in the endosurgical extraction bag, and the first air introducing tube and second air introducing tube are deflated and cinched by the retrieval string.

6. The endosurgical extraction bag according to claim 1, wherein extraction of the large specimen out of the human or animal body is performed using multitude of ways including manual morcellation or power morcellation.

7. The endosurgical extraction bag according to claim 2, wherein insertion/placement of the deflated collection retrieval pouch/bag includes the use of a laparoscopic or a robotic device/arms.

\* \* \* \* \*